US00PP14239P39

(12) United States Plant Patent

Martin et al.

(10) Patent No.: US PP14,239 P3

(45) Date of Patent: Oct. 14, 2003

(54) AVOCADO TREE NAMED '3-29-5'

(50) Latin Name: *Persea americana*
Varietal Denomination: '3-29-5'

(75) Inventors: Gray E. Martin, Fallbrook, CA (US); Berthold O. Bergh, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/096,658

(22) Filed: Mar. 14, 2002

(65) Prior Publication Data

US 2003/0177556 P1 Sep. 18, 2003

(51) Int. Cl.[7] ..... A01H 5/00
(52) U.S. Cl. ..... Plt./200
(58) Field of Search ..... Plt./200

(56) References Cited

U.S. PATENT DOCUMENTS

PP773 P * 12/1947 Sherwood ..... Plt./200

OTHER PUBLICATIONS

UPOV–ROM GTITM Computer Database, 2002/03, GTI Jouve Retrieval Software, citation for 'GEM'.*

Brooks and Olmo, "Register of Fruit and Nut Varieties," 1997, ASHS Press, pp. 134–152.*

* cited by examiner

*Primary Examiner*—Bruce R. Campell
*Assistant Examiner*—Susan B. McCormick
(74) *Attorney, Agent, or Firm*—Burns, Doane, Swecker & Mathis, L.L.P.

(57) ABSTRACT

A new and distinct variety of *Persea americana* tree is provided. A vigorous moderately-spreading upright growth habit is exhibited. The tree is less alternate bearing than the widely-grown 'Hass' variety (non-patented in the United States). The fruit is ellipsoid-shaped, lacks shoulders, is generally black-skinned, is well distributed around the tree, and commonly is larger than that of the 'Hass' variety. The leaves are displayed in a greater quantity than the 'Hass' variety and are similar in appearance to those of the 'Hass' variety. Moderate resistance to Persea mites is exhibited. The variety is suitable for the production of quality avocado crop under commercial growing conditions.

3 Drawing Sheets

Botanical/commercial classification: *Persea americana* Mill./Avocado Tree.
Varietal denomination: cv. '3-29-5'.

SUMMARY OF THE INVENTION

The invention relates to new and distinct variety of Avocado tree that is named '3-29-5'.

The seed that produced the new variety of the present invention was collected in 1985 from open-pollinated avocado trees of the 'Gwen' variety (U.S. Plant Pat. No. 5,298) growing at Riverside and Irvine, Calif. The exact pollen parent is unknown. Seeds were planted in a test planting area at Ventura County, Calif. to produce avocado seedings in the spring of 1986. The resulting seedling plants were observed and studied and a single plant of the new variety was discovered. Had the new variety not been discovered and carefully preserved it would have been lost to mankind. During about 1992 at the Southcoast Research and Extension Center of the University of California located at Irvine, Calif., the new variety was first top worked by grafting on *Persea americana* seedlings. This and subsequent asexual propagation has confirmed that the new variety is stable and that the progeny are formed true to type.

It was found that the new variety of the present invention exhibits the following combination of characteristics:

(a) exhibits a vigorous moderately-spreading upright growth habit, (b) is less alternate bearing than the 'Hass' variety (non-patented in the United States) and fruits well every year, (c) forms ellipsoid-shaped generally black-skinned fruit that is well distributed around the tree which lacks shoulders, commonly is larger than that of the 'Hass' variety, and matures at approximately the same time as the fruit of the 'Hass' variety having yellow-green flesh of excellent eating quality that is free of obvious fibers, (d) forms leaves in greater quantity than the 'Hass' variety that are similar in appearance to those of the 'Hass' variety, and (e) displays moderate resistance to the Persea mite.

The new '3-29-5' variety can be distinguished from all previously known avocado varieties including the 'Hass' variety, the 'Gwen' variety, the 'Sir Prize' variety. (U.S. Plant Pat. No. 9,709), the 'Lamb Hass' variety (U.S. Plant Pat. No. 9,753), and the 'N4(-)5' variety (U.S. Plant patent application No. 10/096,581, filed Mar. 14, 2002) in view of its distinctive combination of characteristics.

The new '3-29-5' variety is believed to be well suited for the production of quality avocados under commercial growing conditions.

BRIEF DESCRIPTION OF THE PHOTOGRAPHS

The accompanying photographs show specimens of the tree and plant parts of the new '3-29-5' variety. The trees had been grafted on seedling *Persea americana* understock.

DETAILED DESCRIPTION

Figure 1:
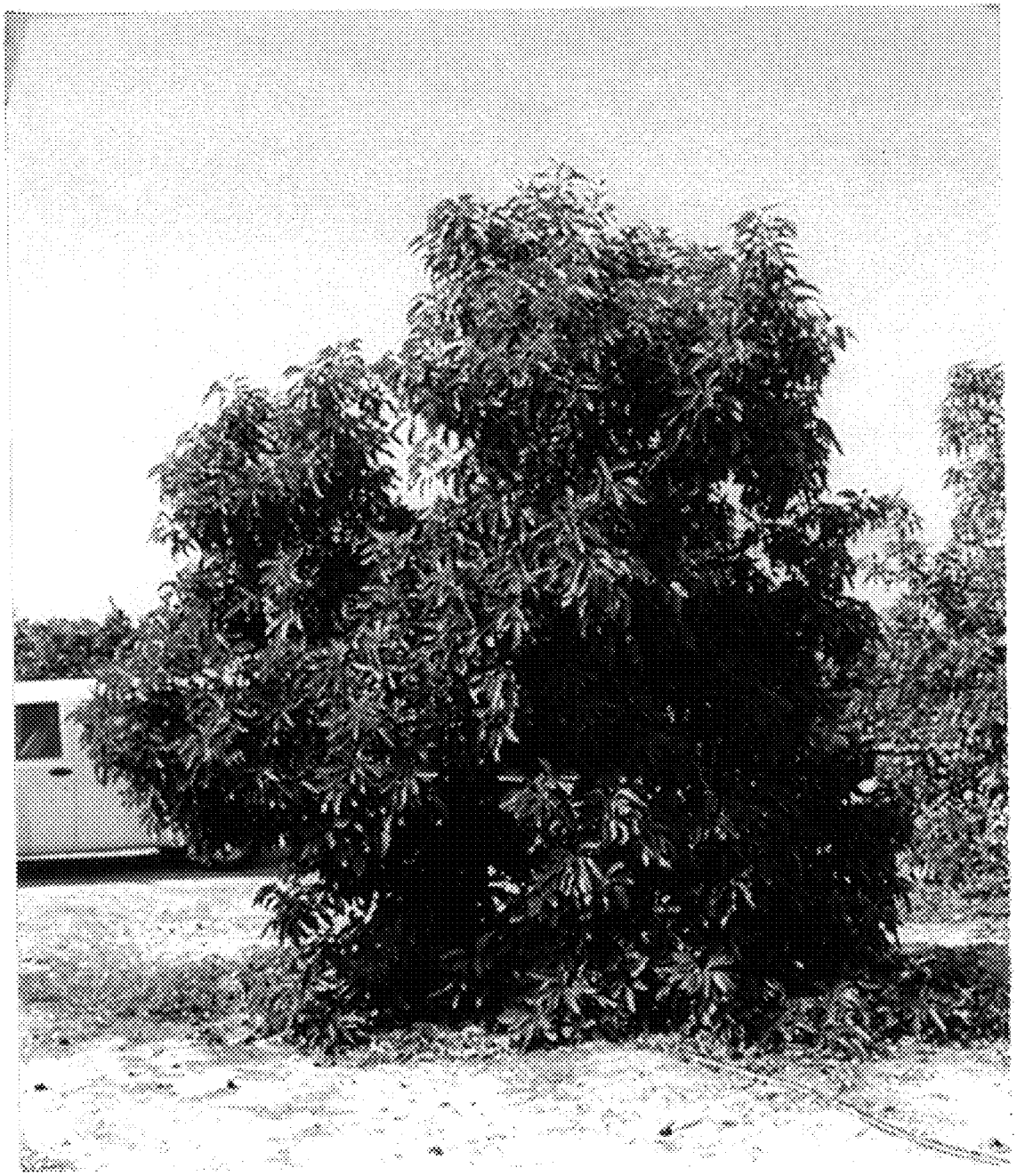
FIG. 1 illustrates a typical six year-old tree of the '3-29-5' variety while growing at Irvine, Calif. The moderately spreading upright growth habit with relatively dense foliage is shown.
Figure 2:
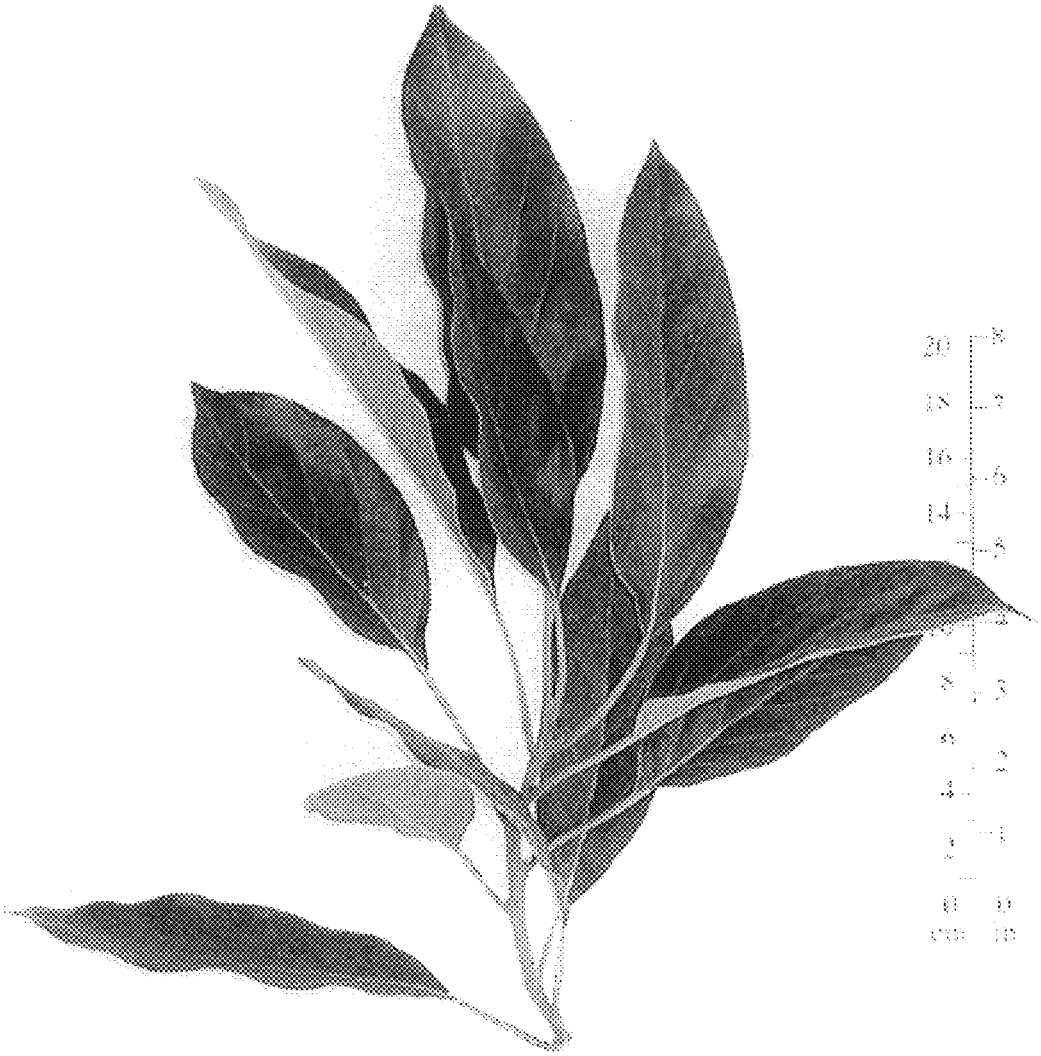
FIG. 2 illustrates typical foliage of the '3-29-5' variety as displayed during the summer. Dimensions in centimeters and inches are shown at the right.

The following is a detailed description of the new '3-29-5' variety. The trees were being grown at experimental orchards of the University of California located at Irvine, Calif., were approximately six years of age, and had been grafted on *Persea americana* seedling understock. When reference to other varieties appears for comparative purposes, such varieties were approximately six years of age with the possible exception of the 'Gwen' variety. The comparative trees of 'Gwen' variety were mature and their exact age was unknown. Color chart information is with reference to The R.H.S. Colour Chart of The Royal Horticultural Society, London, England.

Tree:

*Growth habit.*—Vigorous upright with moderate spreading. This can be compared to spreading for the 'Hass' variety, moderately-spreading for the 'Gwen' variety, and open and spreading for the 'N4(-)5' variety.

*Height.*—Approximately 4.5 m on average. This can be compared to an average height of 4.6 m for the 'Hass' variety, 3.5 m for the 'Gwen' variety, and 4.8 m for the 'N4(-)5' variety.

*Width.*—Approximately 3.5 m on average. This can be compared to an average width of 4.3 m for the 'Hass' variety, 3.3 m for the 'Gwen' variety, and 4.0 m for the 'N4(-)5' variety.

*Bark.*—Substantially identical to that the 'Hass', 'Gwen', and 'N4(-)5' varieties. The new wood is smooth without corky or specially pigmented lenticels. The old wood is corky in appearance as most other avocado varieties and brown, Greyed-Brown Group 199C, in coloration.

*Trunk size.*—Approximately 51.0 cm in circumference on average. This can be compared to an average circumference of 57.6 cm for the 'Hass' variety, 38.9 cm for the 'Gwen' variety, and 64.5 cm for the 'N4(-)5' variety.

Leaves:

*Shape.*—Generally lanceolate with an acute tip and an acute base. The shape is substantially the same as that of the 'Hass' and 'Gwen' varieties. This can be compared to more oval with an acute tip and an acute base for the 'N4(-)5' variety.

*Bearing.*—Alternate.

*Length.*—Approximately 15.4 cm on average. This can be compared to 18.0 cm for the 'Hass' variety, 16.0 cm for the 'Gwen' variety, and 15.4 cm for the 'N4(-)5' variety on average.

*Width.*—Approximately 5.9 cm on average. This can be compared to 6.4 cm for the 'Hass' variety, approximately 5.6 cm for the 'Gwen' variety, and approximately 6.5 cm for the 'N4(-)5' variety on average.

*Leaf weight.*—Approximately 1.78 g on average. This can be compared to approximately 2.67 g for the 'Hass' variety, approximately 1.73 g for the 'Gwen' variety, and approximately 2.17 g for the 'N4(-)5' variety on average.

*Color.*—Near Green Group 137A on the upper surface and near Green Group 137C on the under surface.

*Texture.*—Pubescent when young and smooth and leathery when mature.

*Venation.*—Pinnate and near Green Group 146C in coloration.

*Margin.*—Entire and wavy.

*Petiole.*—Commonly approximately 53.4 mm in length, and approximately 2.3 mm in diameter.

Flowers:

*Type.*—Synchronous dichogamy, and borne in panicles.

*Bud size.*—Approximately 7 mm in length and approximately 3 mm in diameter.

*Bud shape.*—Lanceolate to ovoid.

*Bud color.*—Commonly near Yellow-Green Group 151D.

*Opening.*—Open as female on the morning of the first day, and close in late morning or early afternoon. Such flowers generally remain closed until the afternoon of the second day when they open as male. Such opening sequence commonly is designated as being the "Type A". This flowering behavior is believed to promote cross-pollination since the male and female phases of an individual flower occur at different times. Accordingly, the interplanting of complementary flower types possibly boosts fruit set and yield by making pollen available at the appropriate time. Bees (e.g., European honey bees) can be used to advantage as pollinators.

*Petals.*—Borne in two whorls of three perianth lobes. The petals possess entire margins and the petal coloration is near Yellow-Green Group 151C to 151D.

*Stamen.*—There commonly are nine fertile stamens with each having four pollen chambers, two basal orange nectar glands, and three staminodia. The anthers are tetrathecal.

*Pistil.*—The single pistil has one carpel with one ovule. The ovary is pubescent.

*Pedicel.*—Commonly approximately 6.5 mm in length and approximately 0.6 mm in diameter. The coloration is near Yellow-Green Group 151C.

Fruit:

*Pick dates.*—Commonly March to July or August. This compares to February to July or August for the 'Hass' variety, late February or March into June for the 'Gwen' variety, and fall into early winter for the 'N4(-)5' variety.

*Bearing.*—Less alternate bearing than the 'Hass' variety, and commonly fruits well every year. The fruit is well distributed around the tree and tends to be protected inside the leaf canopy.

*Shape.*—Ellipsoid. The 'Hass' fruit configuration has been found to vary from ellipsoid to obovate from year to year. The 'Gwen' and 'N4(-)5' fruit configuration is generally inverted high spheroid.

*Base.*—Inflated.

*Apex.*—Rounded.

*Size.*—Generally larger than that of the 'Hass' variety. An average fruit weight was found to be 235 g. This can be compared to 204 g for the 'Hass' variety, 210 g for the 'Gwen' variety, and 232 g for the 'N4(-)5' variety. The fruit commonly is approximately 101 mm in length and approximately 77 mm in diameter.

Figure 3:
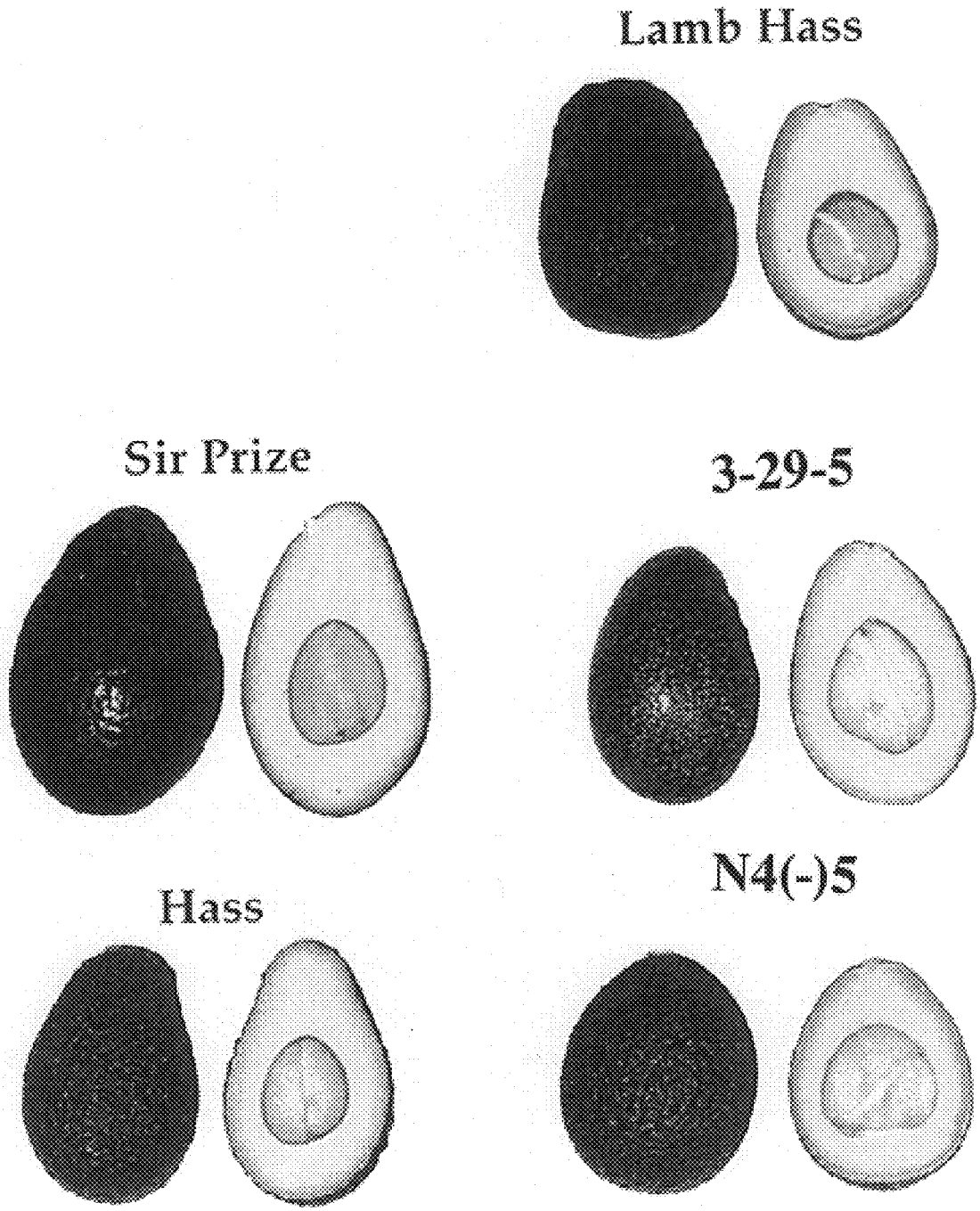
FIG. 3 illustrates typical external and internal views of the fruit of the '3-29-5' variety at the right center. For comparative purposes the fruit of the 'Sir Prize', 'Hass', 'Lamb Hass' and 'N4(-5)' varieties also is included.

*Skin color.*—Very attractive and generally black when soft with numerous light yellow-green lenticels (as illustrated in FIG. 3). With reference to The R.H.S. Colour Chart the skin commonly is near Green Group 137A with lenticels of Yellow-Green Group 146D when hard, and Purple Group 79B to near black with lenticels of Purple Group 79D when soft.

*Flesh color.*—Yellow-green (Yellow Green Group 154C) with more green towards the skin.

*Texture.*—Slightly pebbled. The environment has been found to influence the roughness of the skin surface.

*Percent dry weight.*—This is an indirect measure of the oil content of the avocado fruit. 29.48 percent dry matter on average with a maximum of 36.17 percent on Sep. 4, 2001. This compares to 28.77 percent dry matter on average for 'Hass' with a maximum of 35.01 percent on Jul. 23, 2001, and 22.35 percent dry matter on average for 'N4(-)5' with a maximum of 27.21 percent on Oct. 24, 2001.

*Skin character.*—Pliable.

*Skin thickness.*—Approximately 1.6 mm on average. This can be compared to 1.6 mm for the 'Hass' variety, 1.3 mm for the 'Gwen' variety, and 1.7 mm for the 'N4(-)5' variety on average.

*Skin separation.*—Separates readily and cleanly from the flesh when ripe.

*Seed/skin/flesh ratio by weight.*—Approximately 16:13:71. This can be compared to 14:13:73 for the 'Hass' variety, 18:13:69 for the 'Gwen' variety, and 19:16:65 for the 'N4(-)5' variety.

*Flavor.*—Eating quality is excellent and similar to that of the 'Hass' variety. The flavor is slightly less nutty than the 'Hass' variety and possesses a buttery texture. The flavor of the 'Gwen' fruit also is generally comparable to that of the 'Hass' variety and is considered to be slightly better by some. The fruit flavor of the 'N4(-)5' variety when fully mature possesses a less nutty flavor and tends to possess a bitter/sweet taste when immature.

*Fruit fibers.*—No obvious fruit fibers are apparent.

*Seed shape.*—Broadly ovate. This compares to variable mostly ellipsoid for the 'Hass' variety, and spheroid for the 'Gwen' and 'N4(-)5' varieties.

*Seed weight.*—Approximately 36.0 g on average. This compares to 28.4 g for the 'Hass' variety, 38.8 g for the 'Gwen' variety, and 41.2 g for the 'N4(-)5' variety on average.

*Seed size.*—Commonly approximately 36.1 mm in diameter (longest dimension).

*Seed coat.*—Commonly near Greyed-Orange Group 166B in coloration.

*Cotyledon.*—Commonly near Orange-White Group 159B in coloration.

*Seed ratio.*—Generally comparable to that of the 'Hass' variety.

Productivity: Generally equal to or greater than that of the 'Hass' variety combined with a significantly reduced alternate bearing aspect as previously indicated. Accordingly, more regular high yields are made possible to growers.

Resistance to pests: Moderately resistant to the Persea mite and such resistance is believed to be greater than that of the 'Hass' variety and less than that of the 'Lamb Hass' variety.

Hardiness: Generally comparable to that of the 'Hass' variety. For comparative purposes the 'Gwen' and 'N4(-)5' varieties are believed to be somewhat less hardy.

Market use: The fruit is well suited for the fresh retail and food service markets. Also, the fruit can serve as a source for processed guacamole and other avocado by-products.

We claim:

1. A new and distinct variety of *Persea americana* plant having the following combination of characteristics:

(a) exhibits a vigorous moderately-spreading upright growth habit, (b) is less alternative bearing than the 'Hass' variety (non-patented in the United States) and fruits well every year, (c) forms ellipsoid-shaped generally black-skinned fruit that is well distributed around the tree which lacks shoulders, commonly is larger than that of the 'Hass' variety, and matures at approximately the same time as the fruit of the 'Hass' variety having yellow-green flesh of excellent eating quality that is free of obvious fibers, (d) forms leaves in greater quantity than the 'Hass' variety that are similar in appearance to those of the 'Hass' variety, and (e) displays moderate resistance to the Persea mite;

substantially as illustrated and described.

* * * * *